United States Patent [19]
Pope

[11] Patent Number: 5,496,997
[45] Date of Patent: Mar. 5, 1996

[54] SENSOR INCORPORATING AN OPTICAL FIBER AND A SOLID POROUS INORGANIC MICROSPHERE

[76] Inventor: Edward J. A. Pope, 447 Lorenzo Dr., Agoura, Calif. 91301

[21] Appl. No.: 176,522

[22] Filed: Jan. 3, 1994

[51] Int. Cl.$^6$ ..................................... H01J 5/16
[52] U.S. Cl. ................... 250/227.21; 422/82.06; 250/461.1
[58] Field of Search ............................ 250/227.21, 461.1, 250/458.1; 356/317, 318, 417, 319; 422/82.05, 82.06, 82.07, 82.09, 82.11; 428/402–407

[56] References Cited

U.S. PATENT DOCUMENTS

| | | | |
|---|---|---|---|
| 4,132,560 | 1/1979 | Marquisee et al. | 106/288 B |
| 4,269,648 | 5/1981 | Dakss et al. | 156/293 |
| 4,663,277 | 5/1987 | Wang | 435/5 |
| 4,743,545 | 5/1988 | Torobin | 435/41 |
| 4,895,445 | 1/1990 | Granger | 356/328 |
| 4,939,376 | 7/1990 | Woodruff et al. | 250/554 |
| 5,051,595 | 9/1991 | Kern et al. | 250/458.1 |
| 5,096,671 | 3/1992 | Kane et al. | 422/82.06 |
| 5,102,625 | 4/1992 | Milo | 250/461.1 |
| 5,138,153 | 8/1992 | Gergely et al. | 250/227.21 |
| 5,151,603 | 9/1992 | Nakamura | 250/458.1 |
| 5,173,432 | 12/1992 | Lefkowitz et al. | 250/458.1 |
| 5,200,615 | 4/1993 | Hopenfeld | 250/302 |
| 5,320,814 | 6/1994 | Walt et al. | 422/82.07 |

Primary Examiner—Stephone B. Allen
Attorney, Agent, or Firm—W. Edward Johansen

[57] ABSTRACT

The invention is a sensor which includes a porous microsphere and an optical fiber which having a proximal end and a distal end. The distal end of the optical fiber is coupled to the porous microsphere by an adhesive material. The porous microsphere is doped with a dopant. The dopant may be either an organic dye or an inorganic ion. A sensing apparatus includes the sensor, a spectrophotometer and a source of light. The spectrophotometer is coupled to the proximal end of the optical fiber. The source of light causes either the organic dye or the inorganic ion to fluoresce.

17 Claims, 2 Drawing Sheets

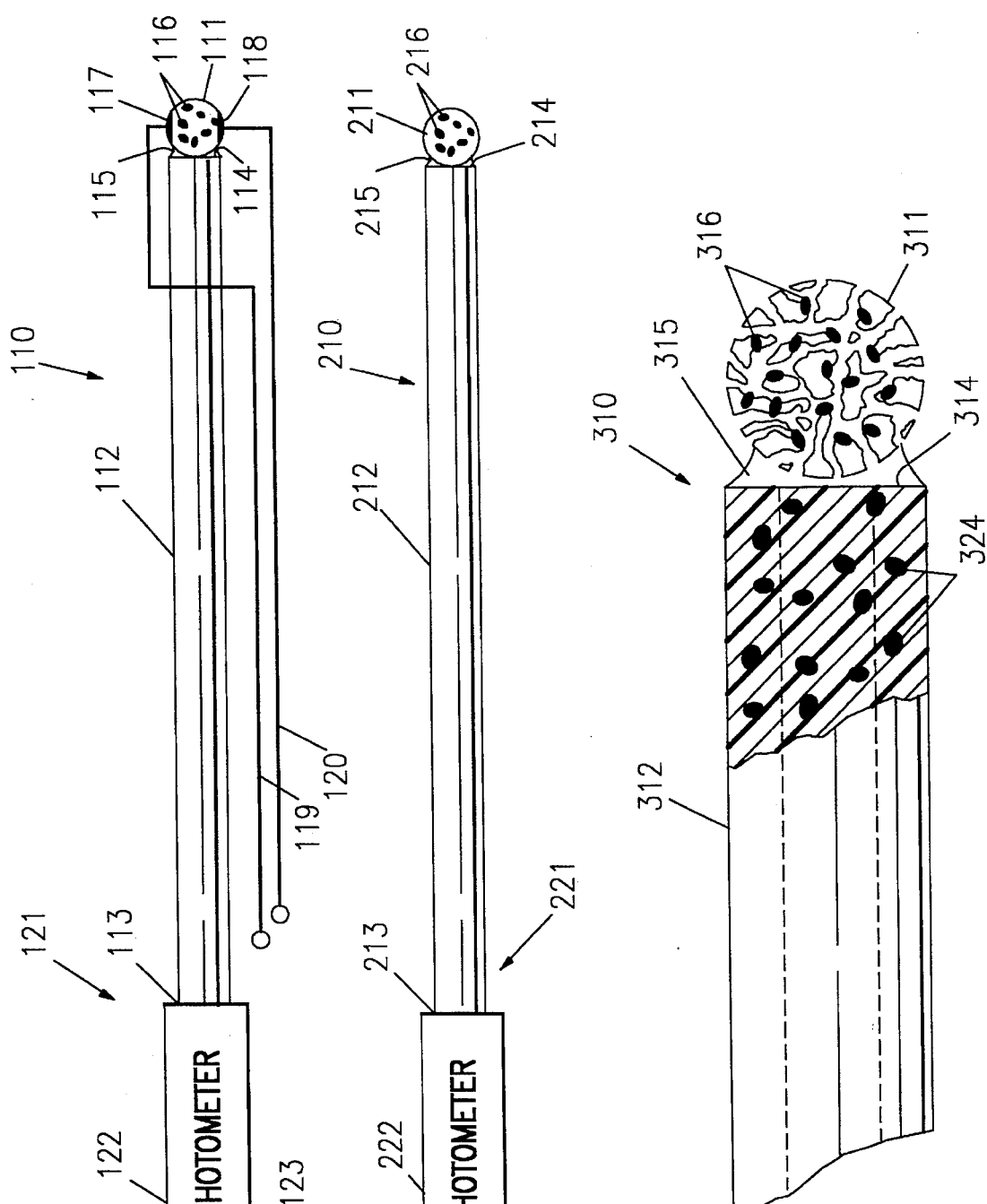

SENSOR INCORPORATING AN OPTICAL FIBER AND A SOLID POROUS INORGANIC MICROSPHERE

BACKGROUND OF THE INVENTION

The field of the invention is sensors incorporating an optical fiber and a microsphere.

U.S. Pat. No. 4,269,648 teaches a microsphere bead coupling lens which can be mounted onto an end of an optical fiber after the end is initially prepared by cleaning and cleavage. An adhesive is first applied to the cleaved end. The applied adhesive end of the optical fiber is then approximately centered over a microsphere bead to be mounted. The fiber is lowered until the adhesive on the end contacts the bead. The fiber is then raised whereby the adhesive on the end holds onto the bead by surface tension so that the bead gets picked up as the fiber is raised; and, due to the combination of surface tension and gravity, the bead lens is moved by the adhesive until the lens is aligned with, or very close to, the central axis of the fiber. Subsequently, the adhesive on the fiber end is cured by either ultraviolet-curing or heat-curing.

U.S. Pat. No. 4,965,701 teaches an illumination curtain in which a support housing includes a spaced series of downwardly descending tubular members receiving therewithin electrical transmission line in communication with spaced illumination bulbs mounted within translucent spheres. The translucent spheres are mounted onto the tubing members at spaced intervals therealong. The tubular members may encase a circuitous optical fiber with a rear terminal end aligned with an opening of an egg-shaped housing containing an illumination bulb therewithin to provide an enhanced visual effect of the illumination curtain.

U.S. Pat. No. 4,965,091 teaches a sol-gel procedure is described for making display devices with luminescent films. The procedure typically involves hydrolysis and polymerization of an organometallic compound together with selected luminescent ions, and coating of a substrate and then heat treatment to form a polycrystalline layer.

U.S. Pat. No. 4,785,814 teaches an optical probe which is for use in measuring pH and oxygen content in blood in a blood vessel within a living body and which includes an optical fiber, a membrane and a plurality of microspheres. The optical fiber is elongated and flexible and has a proximal end and a distal end which is adapted to be inserted into a blood vessel. The membrane is secured to the distal end of the optical fiber and receives light therefrom and returns light therethrough to the proximal end. The membrane is constructed of hydrophilic porous material containing a pH sensitive dye. The microspheres are embedded in and carried by the membrane. The microspheres are constructed of a hydrophobic material. Each microsphere carries a fluorescent dye quenchable with oxygen. Consequently, when light is supplied to the proximal end of the optical fiber, it is conveyed to the membrane. This causes the pH sensitive dye to react and light is conveyed through the optical fiber having an intensity level indicative of the pH level in the blood. The oxygen sensitive dye fluoresces and light is transmitted to the proximal end of an intensity which varies with the partial pressure of oxygen.

U.S. Pat. No. 4,939,376 teaches a light collection device which is for use in a flame emission detection system such as an on-line, real-time alkali concentration process stream monitor and which includes a sphere coated on its interior with a highly diffuse reflective paint which is positioned over a flame emission source, and one or more fiber optic cables which transfer the light generated at the interior of the sphere to a detector. The diffuse scattering of the light emitted by the flame uniformly distributes the light in the sphere. The light collection device provides enhanced sensitivity and reduces the noise associated with flame emission detectors, and can achieve substantial improvements in alkali detection levels.

U.S. Pat. No. 5,051,595 teaches a fiber optic flame detection and temperature measuring system which includes an optical fiber having a lens at a distal end to direct radiation from a fire into the optical fiber to a radiation detector. The optical fiber is doped with a material which has been selected for its temperature dependent fluorescent emission characteristics.

U.S. Pat. No. 5,176,882 teaches an optical fiber which is used in conjunction with a sensor which is capable of sensing more than one analyte. A doped polymer is formed utilizing a hydrophilic polymer which immobilizes a pH sensitive dye and a potassium sensistive fluorescence dye.

U.S. Pat. No. 4,921,788 teaches a kit for performing a competitive immunoassay which utilizes nucleic acid oligonucleotide chains for the detection of analytes, such as drugs, substances of abuse, hormones, poisons, organic compounds, peptides, proteins and the like. The kit includes a hapten-oligonucleotide complex, a complementary oligonculeotide chain for conjugating with the hapten-oligonucleotide complex, an antibody specific for the hapten and a flourescent label such as ethidium bromide having an affinity for nucleic acid duplexes formed from the hapten-oligonucleotide complex and the complementary oligonucleotide chain. A detector for detecting the presence of the florescent label such as a U. V. transilluminator, U. V. lightbox and fluorescence spectrophotometer is utilized to detect color intensity and fluorescence of the dye. The method can be performed in solution, or on a solid "dipstick" on which the reagents for the immunoassay have been immobilized.

U.S. Pat. No. 4,663,277 teaches a virus detection method in which viruses are detected by an immunoassay method in which an extended solid phase coated with antiviral antibody is employed to bind and remove virions from a specimen by forming an immuno-complex with antigens of the virions. A mobile solid phase includes a dispersion of microspheres coated with the antiviral antibody is used to bind the microspheres to antigens associated with the immuno-complex, and the presence of bound microspheres is detected. The detection sensitivity is amplified by the ability to more readily detect the microspheres, which may be dyed or labelled. The extended solid phase advantageously may be in the form of a dipstick which can be easily contacted with the specimen. A virus detection kit provides the extended solid phase and mobile solid phases, each coated with antiviral antibodies.

U.S. Pat. No. 4,983,369 a process for producing highly uniform microspheres of silica having an average diameter of 0.1–10 microns from the hydrolysis of a silica precursor, such as tetraalkoxysilanes, which is characterized by employing precursor solutions and feed rates which initially yield a two-phase reaction mixture.

U.S. Pat. No. 4,943,425 teaches a method of making high purity, dense silica of large particle size. Tetraethylorthosilicate is mixed with ethanol and is added to a dilute acid solution having a pH of about 2.25. The resulting solution is digested for about 5 hours, then 2N ammonium hydroxide is added to form a gel at a pH of 8.5. The gel is screened through an 18–20 mesh screen, vacuum baked, calcined in an oxygen atmosphere and finally heated to about 1200° C. in air to form a large particle size, high purity, dense silica.

U.S. Pat. No. 4,132,560 teaches a pigmented silica microsphere which has an average diameter from 2 to 100 microns and which consists essentially of from 10% to 70% by weight of particulate pigment, dispersed throughout a microporous silica matrix and, optionally, containing a coating of dense amorphous silica. The microspheres are produced by acidifying a water-in-oil emulsion. The pigmented silica microspheres are particularly useful as opacifying agents for coating compositions and as fillers for paper.

U.S. Pat. No. 4,677,138 teaches a high yield process for producing homopolymeric polyaldehyde microspheres which can be prepared in yields of up to about 90% by preparing an aqueous solution consisting essentially of a suitable concentration of an alpha/beta-ethylenically unsaturated aldehyde and a suitable concentration of an appropriate surfactant under suitable conditions such that the surfactant has a net electrostatic charge. The solution, which may also contain a ferrofluidic material, fluorescent dye or additional solvent, is then irradiated under an inert atmosphere with a sufficient dose of gamma radiation to effect polymerization and the monodisperse homopolymeric polyaldehyde microspheres so produced are recovered.

U.S. Pat. No. 4,991,150 teaches a stress sensing material, either piezoelectric or ferroelectric, which is in intimate electrical communication with an electroluminescent material in order to produce light at an amplitude dependent on the stress applied to the stress sensing material. The light signal is transmitted from the electroluminescent material by an optical fiber to an optical signal detector. The electroluminescent material includes a light emitting diode as a small electrical short circuit load across two otherwise insulated faces of a piezoelectric or ferroelectric element.

U.S. Pat. No. 4,997,597 teaches a solid state radioluminescent composition for light source which includes an optically clear polymer organic matrix containing tritiated organic materials and dyes capable of "red" shifting primary scintillation emissions from the polymer matrix. The tritiated organic materials are made by reducing, with tritium, an unsaturated organic compound that prior to reduction contains olefinic or alkynylic bonds.

U.S. Pat. No. 4,927,578 teaches virtually uncrosslinked polyacetylenes in film form are prepared by polymerization of acetylene using a liquid catalyst system consisting of an organicaluminum compound and a titanate in the form of a solution in a viscous inert liquid on a substrate to which the catalyst solution is applied, by a process in which, after the polymerization, the polymer is treated with a strong reducing agent which is inert to the organoaluminum catalyst component, the polymer is, if desired, oriented and is freed from residual catalyst and reducing agent by washing with a liquid, doped with a strong electron acceptor or electron donor in a conventional manner to increase the conductivity and dried, and the materials thus obtained are, if desired, covered with a layer or sheath of nonconductive material.

U.S. Pat. No. 4,968,524 teaches an organic substance which has a polyacetylene linkage exhibiting electrical conductivity and nonlinear optical effect. A process for producing the organic substance having a polyacetylene linkage includes the steps of immersing a substrate having a hydrophilic surface in a solution of a substance containing an acetylene group and a chlorosilane group dissolved in a nonaqueous organic solvent, thereby subjecting the substance containing an acetylene group and a chlorosilane group to chemical adsorption on the surface of the substrate, subjecting the substance to polymerization reaction by the use of radiation such as X-rays, electron beams, gamma-rays, or the like, and thereby producing a polyacetylene.

U.S. Pat. No. 4,906,570 teaches modified polymers which are based on polyvinylene carbonate and/or polyhydroxymethylene containing covalently bonded units which are derived from particular alkoxylated compounds. Polymerization is carried out in the presence of the alkoxylated compounds and a particular dispersion stabilizer. The modified polymer is suitable as a carrier for biologically active substances or for affinity chromatography.

U.S. Pat. No. 4,895,445 teaches a spectrophotometer for operating in the reflection or transmission mode includes a collecting lens for directing non-collimated light from the sample being analyzed onto a diffraction grating. An imaging lens focuses diffracted light onto an array of sensors. Because the collecting lens directs non-collimated light at the grating, a substantially linear spectrum can be imaged on the array.

U.S. Pat. No. 4,920,056 teaches an apparatus for automatic microbatch reaction including a reactor having a reaction chamber, such as a 1.5 milliliter plastic centrifuge tube having a conical bottom. An automatically actuated injection valve is used to inject less than 1 milliliter of a sample into the reaction chamber. One or more automatically actuated reagent valves are used to introduce respective pressurized reagents into the reaction chamber to process the sample. The volume of the reagent(s) introduced into the reaction chamber is less than 1 milliliter and controlled by the on time of the respective reagent valve. The automatically actuated valves are controlled by a computer based timer. A sensor positioned in the chamber, such as a pH electrode, can be used to analyze the processed sample in place or the processed sample can be analyzed by flowing it from the reaction chamber through a flow-through detector, such as a flow-through spectrophotometer.

U.S. Pat. No. 4,952,817 teaches a test system in a stand-alone chassis without a power cord. The testing subsystem, such as a spectrophotometer is microprocessor-controlled, and the microprocessor is disconnected from the battery during normal operation. An ancillary integrated circuit controls the power supply to the microprocessor, and periodically powers up a proximity sensor subsystem, such as a photodiode/LED pair, without powering up the microprocessor. The ancillary circuit powers up the microprocessor IF the proximity sensor subsystem, after being activated, indicates that a sample has been inserted by a user. The microprocessor can then operate the testing subsystem, and provide output data to a display driver accordingly.

U.S. Pat. No. 4,931,646 teaches a multichannel coincidence nuclear detector system for spectral charactertion of nuclear radiation sources at a remote location. The system is designed to detect and classify the radiation source in unfriendly territory and to provide a radio link back to a friendly receiver user station. The sensing elements are comprised of a plurality of plastic scintillator fiber sensors which may be several meters long and with each fiber having a different spectral sensitivity to gamma and neutron sources. Each of the scintillator fibers is connected to a transmitting optical fiber which may be 1 kilometer or more in length. The plurality of optical fibers transmit the optical signal generated by the radiation from a nuclear source impinging on the scintillator fibers to an electronic system. The electronic system is a sealed self contained battery operated device which includes a photomuliplier detector and microprocessor based signal processing and data storage. The microprocessor compares the input signals from each scintillator fiber and determines the energy source. The data is stored in the microprocessor and may be interrogated by a radio frequency link to at a receiver station many kilometers away. The fiber sensors, optical fibers, and the electronics system including a transmitting antenna are all covertly positioned to prevent being observed by an unauthorized person.

An article, entitled "Sol-Gel Optical pH Sensors," published in the *Proceedings of the Society of Photo-Optic Instrumentation Engineers,* Volume 1758, Sol-Gel Optics II, pages 464–475, discloses that a sol-gel process for preparing a thin film of amorphous and transparent oxide materials doped with fluorescein dye. The thin film is placed onto a flat glass substrate. The thin film and the flat glass substrate form a pH sensor.

SUMMARY OF THE INVENTION

The present invention is directed to a sensor incorporating an optical fiber which has a proximal end and a distal end.

In a first aspect of the invention the sensor includes a porous microsphere which is coupled to the distal end of the optical fiber.

In a second aspect of the invention the microsphere is doped with an organic dye.

In a third aspect of the invention the microsphere is doped with an inorganic ion.

In a fourth aspect of the invention the microsphere is doped with an electroluminescent dye. The sensor also includes a pair of electrodes and a pair of conductors.

In a fifth aspect of the invention the microsphere is doped with a radioluminescent dye.

In a sixth aspect of the invention a non-porous microsphere is coupled to the distal end of the optical fiber and is doped with a radioluminescent dye.

In a seventh aspect of the invention the optical fiber is doped with an organic dye.

In an eighth aspect of the invention the optical fiber is doped with an inorganic ion.

In a ninth aspect of the invention the optical fiber is doped with an electroluminescent dye.

In a tenth aspect of the invention the optical fiber is doped with a radioluminescent dye.

In an eleventh aspect of the invention a spectrophotometer is coupled to the proximal end of the optical fiber.

Other aspects and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

DESCRIPTION OF THE DRAWINGS

FIG. 3 is a schematic drawing of a sensing apparatus which includes a sensor according to a second embodiment, a pair of electrodes, a pair of conductors, a source of electrical energy and a spectrophotometer.

FIG. 4 is a schematic drawing of a sensing apparatus which includes a sensor according to a third embodiment and a spectrophotometer.

FIG. 5 is a longitudinal view in partial cross-section of a sensor incorporating an optical fiber and a microsphere according to the fourth embodiment.

DESCRIPTION OF THE PREFERRED EMBODIMENT

Figure 1:
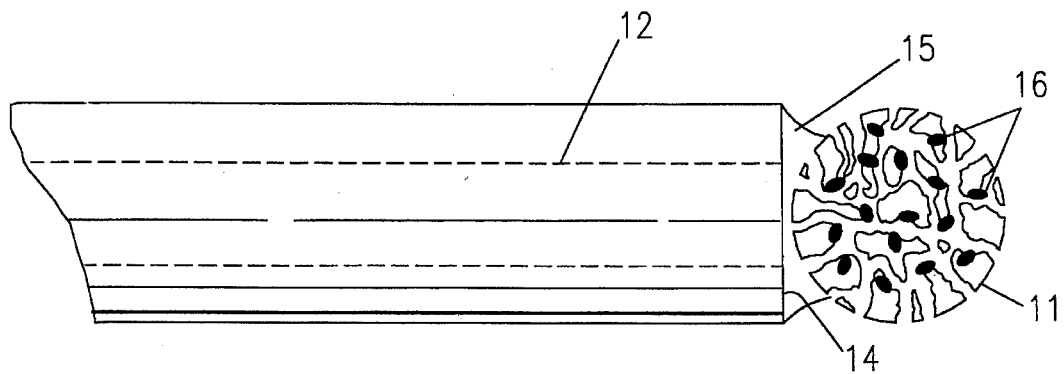
FIG. 1 is a longitudinal view in partial cross-section of a sensor incorporating an optical fiber and a microsphere according to the first embodiment.
Figure 2:
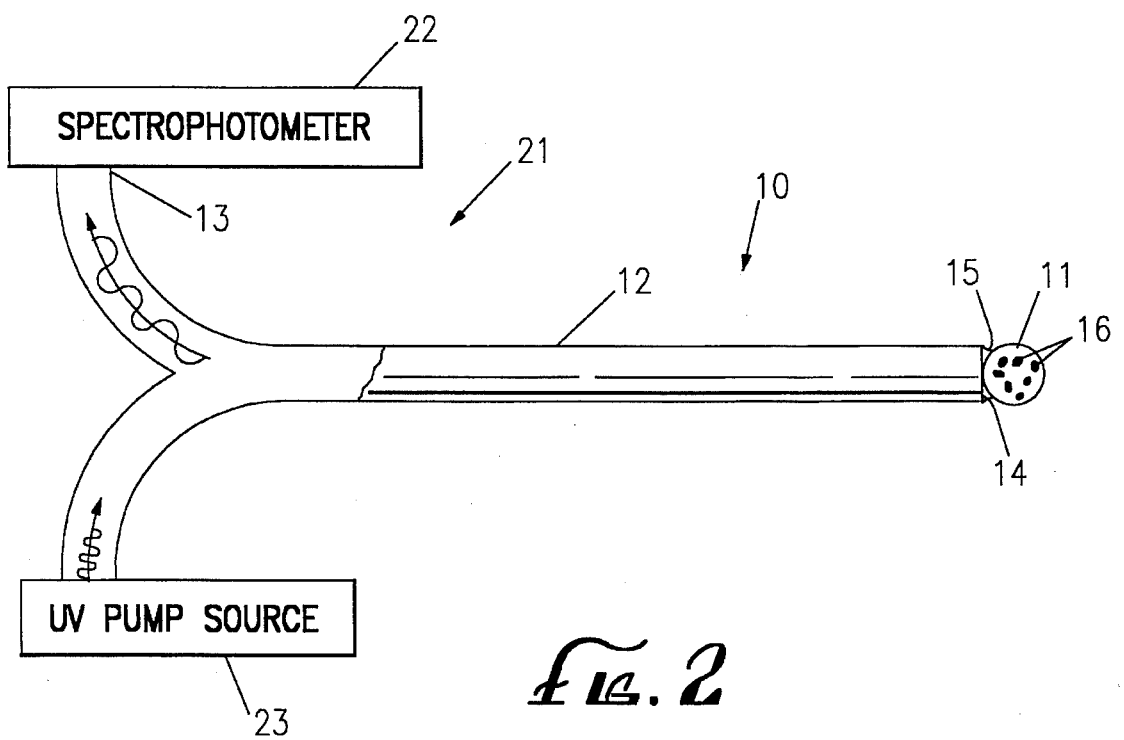
FIG. 2 is a schematic drawing of a sensing apparatus which includes the sensor of FIG. 1, a source of light and a spectrophotometer.

Referring to FIG. 1 in conjunction with FIG. 2 a sensor 10 includes a porous microsphere 11 and an optical fiber 12 which has a proximal end 13 and a distal end 14. The distal end 14 of the optical fiber 12 is coupled to the porous microsphere 11 by an adhesive material 15. The porous microsphere 11 is doped with a dopant 16. The dopant 16 may be either an organic dye or an inorganic ion. Additional dopants may be added. The microsphere 10 may be formed out of either an amorphous ceramic, such as silica, alumina and titania, or an organic polymer, such as polyethylene, polystyrene and polypropylene. The organic dopant may be selected from a group consisting of rhodamine-6G, rhodamine-B, fluorescein, coumarin-120, coumarin-314T and thionin. The inorganic dopant may be selected from a group consisting of europium $3^+$, uranium, neodymium, erbium and uranium-sensitized europium ions. The dopant 16 may also be an organic indicator dye, such as methyl violet and emeraldine green.

The process for synthesizing amorphous silica microspheres with fluorescence behavior includes the steps of placing into a container an organosilicon precursor and a highly acidic solution, adding a dopant and stirring the organosilicon precursor and the highly acidic solution at a stirring rate sufficient to form droplets of the organosilicon precursor in the highly acidic solution. Water in the highly acidic solution hydrolizes the droplets of the organosilicon precursor to form amorphous silica microspheres. The stirring rate is in the range between 8 Hz to 50 Hz. The highly acidic solution has a molar concentration in the range of 0.05 to 2.5. The organosilicon precursor and the highly acidic solution are immiscible. The volumetric ratio of the organosilicon precursor to the highly acidic solution is in the range from 8 to 1 to 18 to 1. The organosilicon precursor is selected from a group consisting of tetraethoxysilane (TEOS), tetrabutoxysilane (TBOS), tetramethoxysilane (TMOS) and tetrapropoxysilane (TPOS). The highly acidic solution is selected from a group consisting of nitric acid ($HNO_3$) and hydrochloric acid (HCl). The dopant is selected from a group consisting of rhodamine-6G, rhodamine-B, europium $3^+$, fluorescein, coumarin-120, coumarin-314T, thionin, uranium and uranium-sensitized europium. The logarithium-plot of the average diameter of the amorphous silica microsphere 10 versus the inverse stirring frequency is linear.

Referring to FIG. 2 a sensing apparatus 21 includes the sensor 10, a spectrophotometer 22 and a source 23 of light. The spectrophotometer 22 is coupled to the proximal end 13 of the optical fiber 12. The source 23 of light causes either the organic dye or the inorganic ion to fluoresce.

In another embodiment the source 23 of light may provide white light which causes either the organic dye or the inorganic ion to selectively reflect a portion of the white light according to its absorptive and reflective spectral characteristics. The environment in which the sensor 10 is placed alters the absorptive and reflective spectral characteristics of these dopant.

Referring to FIG. 1 in conjunction with FIG. 3 a sensor 110 includes a porous microsphere 111 and an optical fiber 112 which has a proximal end 113 and a distal end 114. The distal end 114 of the optical fiber 112 is coupled to the porous microsphere 111 by an adhesive material 115. The porous microsphere 111 is doped with a dopant 116. The dopant 116 is an electroluminescent dye. Additional dopants may be added. The sensor 116 also includes a first electrode 117, a second electrode 118, a first conductor 119 and a second conductor 120. The first electrode 117 is coupled to the porous microsphere 111. The second electrode 118 is coupled to the porous microsphere 111 and is disposed parallel to the first electrode 117. The first conductor 119 is coupled to the first electrode 117. The second conductor 120 is coupled to the second electrode 118.

Referring to FIG. 3 a sensing apparatus 121 includes the sensor 110 a spectrophotometer 122 and source 123 of electrical energy. The spectrophotometer 122 is coupled to the proximal end 113 of the optical fiber 112. The source 123 of electrical energy causes the electroluminescent dye to fluoresce.

Referring to FIG. 1 in conjunction with FIG. 4 a sensor 210 includes a microsphere 211, either porous or nonporous, and an optical fiber 212 which has a proximal end 213 and a distal end 214. The distal end 214 of the optical fiber is coupled to the microsphere 211 by an adhesive material 215. The microsphere 211 is doped with a dopant 216. The dopant 216 is a radioluminescent dye. Additional dopants may be added.

Referring to FIG. 4 a sensing apparatus 221 includes the sensor 210 and a spectrophotometer 222. The spectrophotometer 222 is coupled to the proximal end 213 of the optical fiber 212. Radiation causes the radioluminescent dye to fluoresce.

Referring to FIG. 1 in conjunction with FIG. 5 a sensor 310 includes a microsphere 311, either porous or nonporous, and an optical fiber 312 which has a proximal end and a distal end 314. The distal end 314 of the optical fiber 312 is coupled to the microsphere 311 by an adhesive material 315. The microsphere 311 is doped with a dopant 316. The dopant 316 may be an organic dye, an inorganic ion, an electroluminescent dye or a radioluminescent dye. Additional dopants may be added. The optical fiber 312 is doped with a dopant 324. The dopant 324 may be an organic dye, an inorganic ion, an electroluminescent dye or a radioluminescent dye. Additional dopants may be added A sensing apparatus includes an optically active silica-gel microsphere, a first second optical fiber, a second optical fiber, a source of light and a spectrophotometer. The first optical fiber has a proximal end and a distal end which is coupled to the optically active silica-gel microsphere. The source of light is coupled to the proximal end of the first optical fiber and causes the dopant to fluoresce. The second optical fiber has a proximal end and a distal end which is coupled to the optically active silica-gel microsphere. The spectrophotometer is coupled to the proximal end of the second optical fiber. When the optically active silica-gel microshere is immersed in a biological fluid, a spectrophotometer is able to measure a shift in the fluorescence peak wavelength. The sensing apparatus also includes a container which contains a biological fluid to be tested for either the presence or the absence of an organism. The microsphere is placed in the container and if the organism is present a shift in the fluorescence peak wavelength of the dopant occurs. The spectrophotometer determines if the shift in the fluorescence peak wavelength of the dopant has occurred.

From the foregoing it can be seen that a sensor incorporating an optical fiber and a microsphere has been described. It should be noted that the sketches are not drawn to scale and that distance of and between the figures are not to be considered significant. Accordingly it is intended that the foregoing disclosure and showing made in the drawing shall be considered only as an illustration of the principle of the present invention.

What is claimed is:

1. A sensor comprising:
   a. a solid porous inorganic microsphere; and
   b. an optical fiber having a proximal end and a distal end, said distal end of said optical fiber being coupled to said solid porous inorganic microsphere.

2. A sensor according to claim 1 wherein said solid porous inorganic microsphere is doped with an organic dye.

3. A sensor according to claim 1 wherein said solid porous inorganic microsphere is doped with an inorganic ion.

4. A sensor according to claim 1 wherein said solid porous inorganic microsphere is doped with a radioluminescent dye.

5. A sensor comprising:
   a. a solid non-porous inorganic microsphere which is doped with a radioluminescent dye; and
   b. an optical fiber having a proximal end and a distal end, said distal end of said optical fiber being coupled to said solid non-porous inorganic microsphere.

6. A sensor according to claim 1 wherein said solid porous inorganic microsphere is doped with an electroluminescent dye and wherein said sensor includes:
   a. a first electrode coupled to said solid porous inorganic microsphere;
   b. a second electrode coupled to said solid porous inorganic microsphere and disposed parallel to said first electrode;
   c. a first conductor coupled to said first electrode; and
   d. a second conductor coupled to said second electrode.

7. A sensor according to claim 1 wherein said optical fiber is doped with an organic dye.

8. A sensor according to claim 1 wherein said optical fiber is doped with an inorganic ion.

9. A sensor according to claim 1 wherein said optical fiber is doped with a radioluminescent dye.

10. A sensor according to claim 1 wherein said optical fiber is doped with an electroluminescent dye.

11. A sensing apparatus comprising:
    a. a solid porous inorganic microsphere;
    b. a first optical fiber having a proximal end and a distal end, said distal end of said first optical fiber being coupled to said solid porous inorganic microsphere; and
    c. a spectrophotometer coupled to said proximal end of said first optical fiber.

12. A sensing apparatus according to claim 11 wherein said solid porous inorganic microsphere is doped with an organic dye and wherein said sensing apparatus, includes a source of light which causes said organic dye to fluoresce.

13. A sensing apparatus according to claim 11 wherein said solid porous inorganic microsphere is doped with an inorganic ion and wherein said sensing apparatus includes a source of light which causes said inorganic ion to fluoresce.

14. A sensing apparatus according to claim 11 wherein said solid porous inorganic microsphere is doped with a electroluminescent dye and wherein said sensing apparatus includes:
   a. a first electrode coupled to said solid porous inorganic microsphere;
   b. a second electrode coupled to said solid porous inorganic microsphere and disposed parallel to said first electrode;
   c. a first conductor coupled to said first electrode;
   d. a second conductor coupled to said second electrode;
   e. a source of electrical energy coupled to said first and second conductors to cause said electroluminescent dye to fluoresce.

15. A sensing apparatus according to claim 11 wherein said solid porous inorganic microsphere is doped with a radioluminescent dye.

16. A sensing apparatus comprising:
   a. a solid porous inorganic microsphere which is doped with an organic dye;
   b. a first optical fiber having a proximal end and a distal end, said distal end of said first optical fiber being coupled to said solid porous inorganic microsphere;
   c. a source of light coupled to said proximal end of said first optical fiber, said source of light causing said organic dye to fluoresce;
   d. a second optical fiber having a proximal end and a distal end, said distal end of said second optical fiber being coupled to said porous inorganic microsphere; and
   e. a spectrophotometer coupled to said proximal end of said second optical fiber.

17. A sensing apparatus system according to claim 16 wherein said sensing apparatus includes a container containing a biological fluid to be tested for either the presence or the absence of an organism, said porous inorganic microsphere being placed in said container whereby if the organism is present a shift in the fluorescence peak wavelength of said dopant occurs and said spectrophotometer determines if said shift in the fluorescence peak wavelength of said dopant has occurred.

* * * * *